(12) United States Patent
Larsen

(10) Patent No.: US 10,219,743 B2
(45) Date of Patent: Mar. 5, 2019

(54) MASK HAVING INTEGRATED PHYSIOLOGICAL CONDITION SENSORS

(71) Applicant: Honeywell International Inc., Morristown, NJ (US)

(72) Inventor: Christopher Scott Larsen, Rockford, MN (US)

(73) Assignee: HONEYWELL INTERNATIONAL INC., Morristown, NJ (US)

( * ) Notice: Subject to any disclaimer, the term of this patent is extended or adjusted under 35 U.S.C. 154(b) by 1053 days.

(21) Appl. No.: 13/921,069

(22) Filed: Jun. 18, 2013

(65) Prior Publication Data

US 2014/0005497 A1  Jan. 2, 2014

Related U.S. Application Data

(60) Provisional application No. 61/667,285, filed on Jul. 2, 2012.

(51) Int. Cl.
| | |
|---|---|
| *A61B 5/00* | (2006.01) |
| *A61M 16/06* | (2006.01) |
| *A61B 5/024* | (2006.01) |
| *A61B 5/08* | (2006.01) |
| *A61B 5/01* | (2006.01) |
| *A61B 5/0205* | (2006.01) |

(52) U.S. Cl.
CPC .............. *A61B 5/6803* (2013.01); *A61B 5/01* (2013.01); *A61B 5/024* (2013.01); *A61B 5/0816* (2013.01); *A61B 5/746* (2013.01); *A61M 16/06* (2013.01); *A61B 5/0022* (2013.01); *A61B 5/02055* (2013.01); *A61B 2503/20* (2013.01); *A61B 2562/043* (2013.01); *A61B 2562/164* (2013.01); *A61M 2205/0216* (2013.01); *A61M 2205/502* (2013.01); *A61M 2230/06* (2013.01); *A61M 2230/42* (2013.01); *A61M 2230/50* (2013.01)

(58) Field of Classification Search
CPC . A61B 5/02438; A61B 5/02055; A61B 5/024; A61B 5/6803; A61B 5/6814; A61B 5/0816; A61B 5/746; A61B 2562/043; A61B 2562/164; A61B 2230/06; A61B 2230/42; A61B 2230/50; A61B 5/683; A61B 5/6831; A61M 16/06; A61M 2205/502; A63B 2230/06; A63B 2230/42; A63B 2230/50; A62B 18/00; A62B 18/02; A62B 18/04; A62B 18/08
USPC .......................... 128/206.24, 206.12, 201.24
See application file for complete search history.

(56) References Cited

U.S. PATENT DOCUMENTS

| | | | | |
|---|---|---|---|---|
| 4,875,477 | A * | 10/1989 | Waschke | A61B 5/02438 128/206.21 |
| 6,199,550 | B1 * | 3/2001 | Wiesmann | A62B 9/006 128/202.22 |

(Continued)

OTHER PUBLICATIONS

Finvers, I. G., et al., "Wireless Temporal Arterty Bandage Thermometer", IEEE Biomedical Circuits and Systems Conference (BioCAS 2006), (2006), 166-169.

*Primary Examiner* — Timothy J Neal
*Assistant Examiner* — Aaron B Fairchild
(74) *Attorney, Agent, or Firm* — Alston & Bird LLP

(57) ABSTRACT

The present disclosure relates to a human wearable mask includes a skirt for directly contacting a forehead of a human wearer, a patch with sensors on the skirt to obtain and provide temperature data from the forehead of the human wearer.

13 Claims, 5 Drawing Sheets

(56) References Cited

U.S. PATENT DOCUMENTS

| | | | |
|---|---|---|---|
| 7,296,570 B2* | 11/2007 | Hutchinson | A61F 7/02 128/201.26 |
| 2003/0212315 A1* | 11/2003 | Wiesmann | A61B 5/14551 600/322 |
| 2004/0163648 A1* | 8/2004 | Burton | A61B 5/04085 128/204.21 |
| 2007/0206655 A1* | 9/2007 | Haslett | A61B 5/01 374/141 |
| 2010/0217099 A1* | 8/2010 | LeBoeuf | A61B 5/00 600/301 |

* cited by examiner

MASK HAVING INTEGRATED PHYSIOLOGICAL CONDITION SENSORS

FIELD OF THE INVENTION

The present disclosure relates to a mask. More particularly, the disclosure relates to a mask with a sensor to sense a physiological condition.

BACKGROUND

First responders, soldiers, and other wearers often work in stressful conditions and in hot environments. The protective gear and other equipment can add to the heat and physical stress. Heat related illnesses, such as heat exhaustion and heat stroke, are a very real problem in these environments, and can result in hospitalization or death. By accurately monitoring physiological parameters of the wearer and sending them to a central monitoring station, heat related illnesses or other stresses can be recognized before they become too serious, and preventive action can be taken.

SUMMARY

A human wearable mask includes a skirt for directly contacting a forehead of a human wearer and a sensor on the skirt to obtain and provide temperature data from the forehead of the human wearer.

DETAILED DESCRIPTION

In the following description, reference is made to the accompanying drawings that form a part hereof, and in which is shown by way of illustration specific embodiments which may be practiced. These embodiments are described in sufficient detail to enable those skilled in the art to practice the embodiments, and it is to be understood that other embodiments may be utilized and that structural, logical and electrical changes may be made. The following description of example embodiments is, therefore, not to be taken in a limited sense, and the scope is defined by the appended claims.

The functions or algorithms described herein may be implemented in software or a combination of software and human implemented procedures in one embodiment. The software may consist of computer executable instructions stored on computer readable media such as memory or other type of storage devices. Further, such functions correspond to modules, which are software, hardware, firmware or any combination thereof. Multiple functions may be performed in one or more modules as desired, and the embodiments described are merely examples. The software may be executed on a digital signal processor, application specific integrated circuit (ASIC), microprocessor, or other type of processor operating on a computer system, such as a personal computer, server or other computer system.

Issues encountered with physiological monitoring of wearers include obtaining accurate measurements and doing so in an unobtrusive fashion to ensure wearer use and compliance with monitoring. Such wearers may be in indoor or outdoor activities during which heat stress may occur. Another issue includes sending the data to a decision maker to determine the best course of action to protect the wearer.

The embodiments can monitor body core temperature in a wearer. A patch is placed in contact with skin on the forehead of a wearer to monitor the body core temperature. At least a portion of the patch is in contact with skin over the superficial temporal artery of the wearer. Blood in the superficial temporal artery has a temperature substantially equal to the body core temperature of the wearer.

Figure 1A:
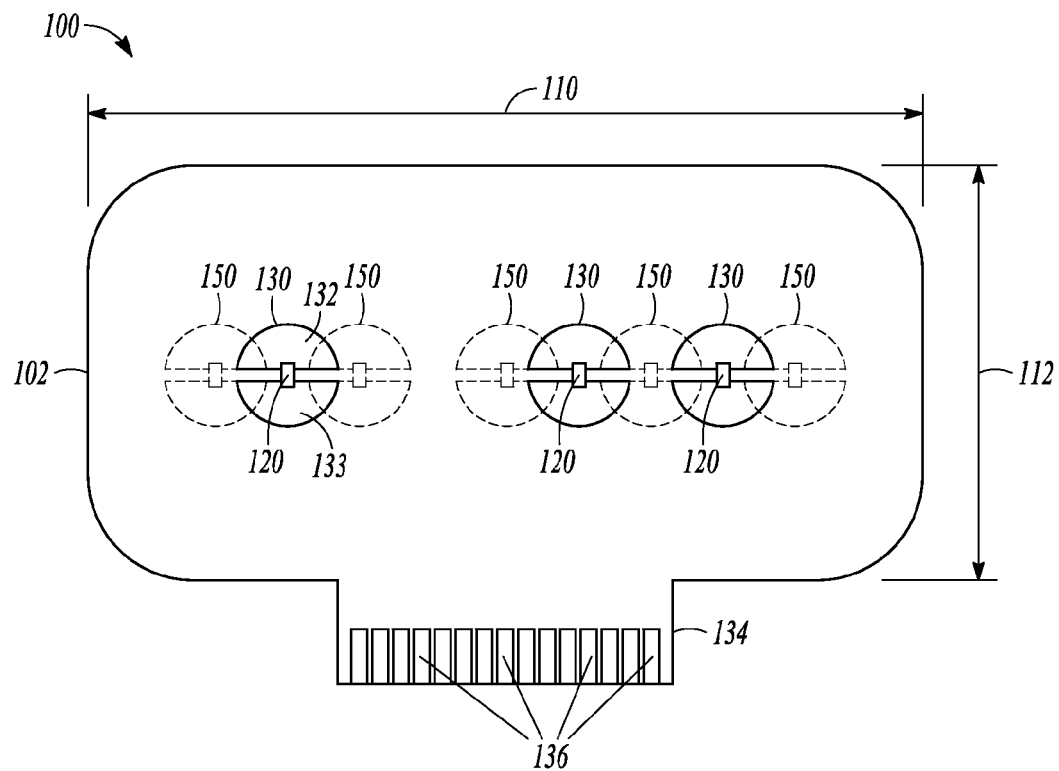
FIG. 1A is a top view of a patch according to an example embodiment.

FIG. 1A is a top view of a patch 100 according to an example embodiment. The patch 100 is substantially rectangular with rounded corners, although it may have another shape suited for placement in a mask. The patch 100 comprises a main body 102 comprising a flexible polyamide or paper or plastic material with integrated circuits and conductive lines or traces and terminals formed thereon (not shown). The main body 102 has a length 110, a width 112 and a thickness (shown in FIG. 1C). The length 110 is approximately 1.5 inches and the width 112 is approximately 1 inch. FIG. 1A illustrates an insulated side of the main body 102 that is fixed to a mask worn by the wearer. The patch 100 includes three thermistors 120 on the insulated side of the main body 102, each thermistor 120 being in thermal contact with a metal disk 130. The insulated side of the main body 102 is embedded in a layer of silicone (not shown). Each metal disk 130 comprises two semicircles of metal 132 and 133. Separate contacts of a thermistor 120 are each in thermal contact with a respective one of the semicircles of metal 132 and 134 that conduct head to the thermistor 120 and are also electrical contacts for the thermistor 120. The terminals of the thermistor 120 can be soldered to the semicircles of metal 132 and 134. Each metal disk 130 can comprise copper with a diameter of approximately five millimeters and a weight of approximately one-half ounces per square foot. The copper may have a different weight according to example embodiments. The metal disks 130 provide thermal conductivity over an area larger than the respective thermistor 120 with which they are in thermal contact. The semicircles of metal 132 and 134 may be squares or rectangles of metal according to example embodiments.

The patch 100 includes a projecting portion 134 that projects from the main body 102. The projecting portion 134 also comprises the flexible polyamide material. The projecting portion 134 includes electrical contacts 136 that may be metal pads to couple signals to and from the patch 100. The electrical contacts 136 may be formed on the main body 102 without the projecting portion 134 according to an example embodiment.

Figure 1B:
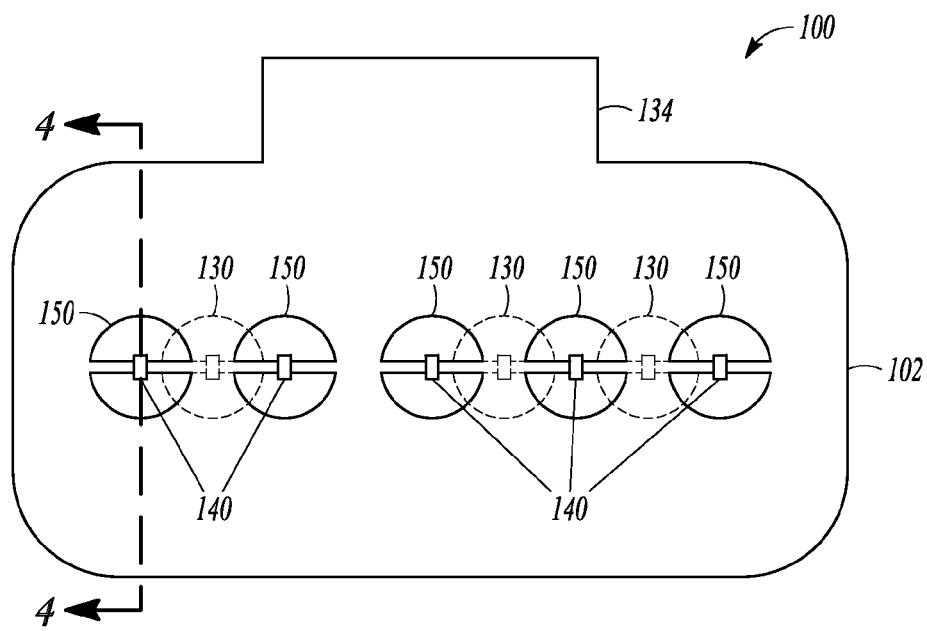
FIG. 1B is a bottom view of the patch shown in FIG. 1A according to an example embodiment.

FIG. 1B is a bottom view of the patch 100 shown in FIG. 1A according to an example embodiment. FIG. 1B illustrates a skin side of the main body 102 to be in contact with the skin of the wearer. The patch 100 includes five thermistors 140 on the skin side of the main body 102, each thermistor 140 being in thermal contact with a metal disk 150. The metal disks 150 may each comprise copper and have a diameter of approximately five millimeters and a weight of approximately one-half ounce per square foot. The copper may have a different weight according to example embodiments. The metal disks 150 provide thermal conductivity over an area larger of the skin of the wearer than the respective thermistor 140 with which they are in thermal contact.

The metal disks 130 and 150 may have a different shape, such as a polygon having three or more edges. Each thermistor 120 and 140 has a negative temperature coefficient (NTC). The thermistors 120 and 140 may alternatively have a positive temperature coefficient (PTC) in example embodiments. Alternatively, a separate thermocouple is integrated into each metal disk 130 and 150.

Figure 1C:
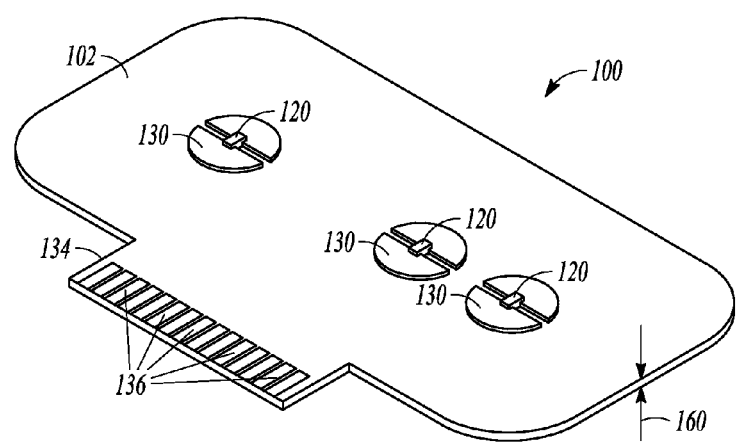
FIG. 1C is an oblique view of the patch shown in FIG. 1A and FIG. 1B according to an example embodiment.

FIG. 1C is an oblique view of the patch 100 shown in FIG. 1A and FIG. 1B according to an example embodiment. The main body 102 has a thickness 160 of approximately 0.012 inches. FIG. 1C illustrates the insulated side of the main body 102 including the thermistors 120 and the metal disks 130 that are near a mask worn by the wearer.

Figure 2:
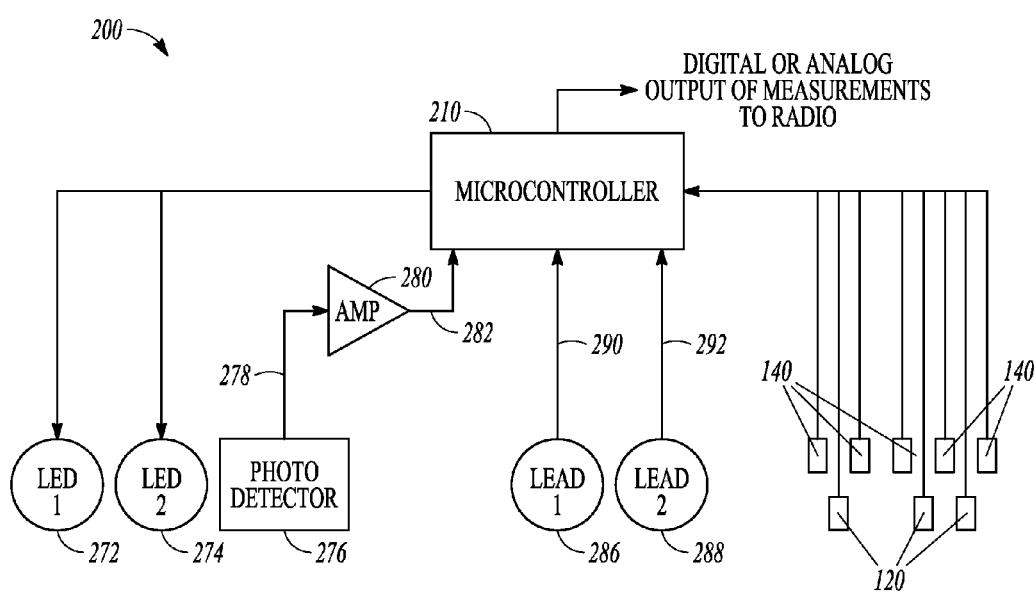
FIG. 2 is a block diagram of circuitry in the patch shown in FIG. 1A, FIG. 1B and FIG. 1C according to an example embodiment.

FIG. 2 is a block diagram of circuitry 200 in the patch 100 shown in FIG. 1A, FIG. 1B and FIG. 1C according to an example embodiment. The circuitry 200 is formed on or in the main body 102. The circuitry 200 includes a microcontroller 210 to receive and analyze signals on separate lines from the thermistors 120 and 140. The thermistors 120 and 140 can generate analog signals representing the temperatures of the metal disks 130 and 150. The microcontroller 210 can digitize the analog signals from the thermistors 120 and 140 into digital data, encode the digital data and transmit the encoded digital data through a wireless transmitter (not shown). The microcontroller 210 can also perform calculations based on the digital data.

The microcontroller 210 is coupled to exchange signals with other sensors. For example, the patch 100 has a pulse oximeter sensor and a galvanic skin response (GSR) sensor. The microcontroller 210 can provide control signals to two light-emitting diodes (LEDs) 272 and 274 in the pulse oximeter sensor to prompt the LEDs 272 and 274 to emit light at different wavelengths. The light passes through tissue to reach a photo detector 276 that can be a photodiode. The photo detector 276 can generate an analog signal on a line 278 to indicate light received from the tissue. The signal on the line 278 can be amplified by an amplifier 280 and provided on a line 282 to the microcontroller 210. The microcontroller 210 can convert the analog signal from the pulse oximeter sensor into digital data and analyze the digital data to estimate the oxygen saturation of blood in the tissue and also a respiration rate of the wearer.

The microcontroller 210 is coupled to receive analog signals from two conductive electrodes 286 and 288 in the GSR sensor on lines 290 and 292, respectively. The microcontroller 210 can convert the analog signals from the electrodes 286 and 288 into digital data and analyze the digital data to estimate an electrical conductance of the skin and a perspiration (sweat) rate of the wearer.

At least one of the metal disks 150 on the skin side of the main body 102 will be in contact with skin over the superficial temporal artery at the body core temperature. The metal disks 130 on the insulated side of the main body 102 may have a temperature between the temperature of the environment and the body core temperature. The microcontroller 210 can perform calculations based on a temperature difference between the metal disks 150 on the skin side of the main body 102 and the metal disks 130 on the insulated side of the main body 102 to estimate the magnitude and direction of energy flow through the patch 100. Thermal energy may flow from the wearer to the insulated side of the main body 102 or from a high-temperature environment to the wearer.

The core temperature Tc of the wearer can be estimated from the following equation:

$$Tc \cong \frac{h_{patch}}{h_{tissue}}(T_s - T_i) + T_s$$

In this equation $T_s$ is the temperature of skin over the temporal artery, $h_{patch}$ is the heat transfer coefficient of the patch 100, $h_{tissue}$ is the heat transfer coefficient of skin over the temporal artery and $T_i$ is the temperature of the thermistor on the insulated side of the patch opposite the wearer's skin 120. Results of the calculations and the data are encoded and transmitted through equipment used by the wearer.

In various embodiments, physiological monitoring is integrated into protective self-contained breathing apparatus (SCBA) or respirator masks that are already used by the wearer can ensure compliance while still obtaining accurate measurements. Several key indicators of heat illnesses are high body core temperature, rapid heart rate, rapid breathing, heavy sweating (or no sweating in the case of heat stroke), and weak pulse (strong pulse in the case of heat stroke). Each of these parameters may be measured through the forehead, allowing integration of one or a plurality of these physiological measurements with the wearer's existing wearable protection equipment (PPE). These measurements can be taken with a few sensors and little inconvenience to the wearer, providing excellent monitoring. The wearer's condition can be sent to a foreman or incident commander to determine the best course of action to protect the wearer.

Physiological measurements may be taken using various sensors. In one embodiment, sensors are integrated into a SCBA mask or respirator and the communication of sensor data is provided over wired or wireless channels.

Figure 3:
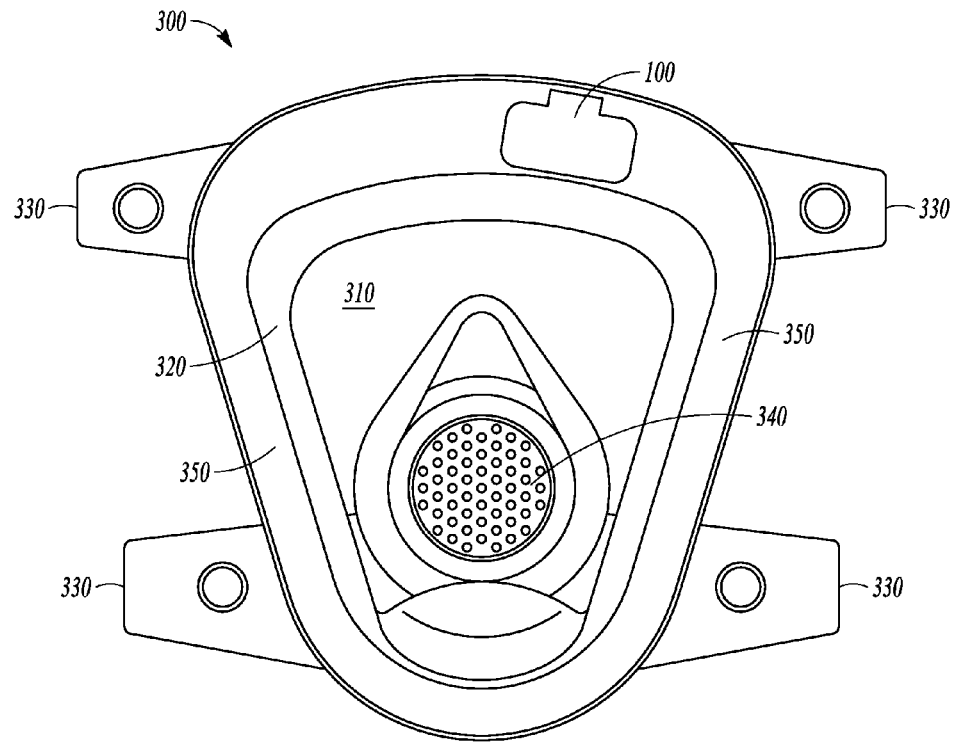
FIG. 3 illustrates a mask according to an example embodiment.

FIG. 3 illustrates a mask 300 according to an example embodiment. The mask 300 can be a SCBA mask or respirator mask. The mask 300 has a substantially transparent visor 310 held in an air-tight fashion by a frame 320. Straps 330 are fixed to the frame 320 and can be wrapped around the head of a wearer to hold the mask 300 in place. A gas conduit 340 in the frame 320 allows the wearer to breathe through the mask 300. The conduit 340 may include one or more filters to filter incoming gas or may be attached to receive gas from a source of gas such as air or oxygen (not shown). The mask 300 has a skirt 350 attached to the frame 320 in an air-tight manner. The skirt 350 is flexible and is attached to the frame 320 along the entire perimeter of the frame 320 and the visor 310. The skirt 350 may form a substantially air-tight seal with the face and forehead of the wearer which is important to prevent toxins from leaking into the space inside the mask 300 between the visor 310 and the wearer. The insulated side of the main body 102 of the patch 100 is affixed to the skirt 350 near the forehead of the wearer wearing the mask 300, and more specifically near the temporal artery of the wearer. More particularly, the silicone on the insulated side of the main body 102 is attached in an air-tight manner to the skirt 350. The skirt 350 may also be formed of silicone, which may reduce cooling, making a skin temperature of the wearer closer to the body core temperature of the wearer. The patch 100 may be embedded in the skirt 350 according to an example embodiment.

By probability, one of the thermistors 140 will be over the temporal artery of the wearer. That thermistor will register the highest skin temperature. The total heat flux through the skin can be measured by another thermistor on the back side of the flex circuit patch. Data from the back side thermistor may be used to correct for any cooling effects of the skin (sweating, wind speed, etc).

The data collected may be communicated to the wearer via indicator lights, displays, or speakers/alarms (not shown). The data may also be communicated to a foreman, fire incident commander, or a central office through wired or wireless channels, possibly including the data channel of existing voice radios, telemetry units such as the PASS unit worn by firefighters, audio modulation of voice channels on radios, or the use of radios specific to this application. The wearer condition can be described as a green-yellow-red indication, formulated by the aggregate of the physiological measurements. This would be done for simplicity of decision making by the foreman, as well as to preserve wearer privacy about their medical condition.

Figure 4:
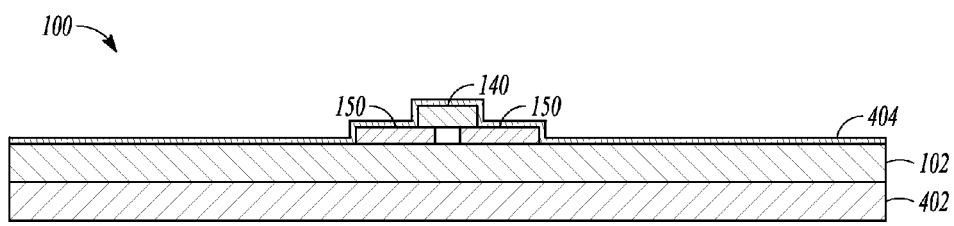
FIG. 4 is a cross-sectional view of the patch shown in FIG. 1A, FIG. 1B and FIG. 1C according to an example embodiment.

FIG. 4 is a cross-sectional view of the patch 100 shown in FIG. 1A, FIG. 1B and FIG. 1C according to an example embodiment. The main body 102 is shown with a metal disk 150 fixed thereto. A thermistor 140 is in thermal contact with both semicircles of the metal disk 150, each of two terminals of the thermistor 140 being in thermal contact with one semicircle of the metal disk 150. The insulated side of the main body 102 is in contact with a tier of silicone 402 to insulate and protect the main body 102. A conformal amount of silicone 404 is formed on the skin side of the main body 102, the thermistor 140 and the metal disk 150 for protection. A conformal coating could be applied instead of the silicone 404 according to an example embodiment.

Figure 5A:
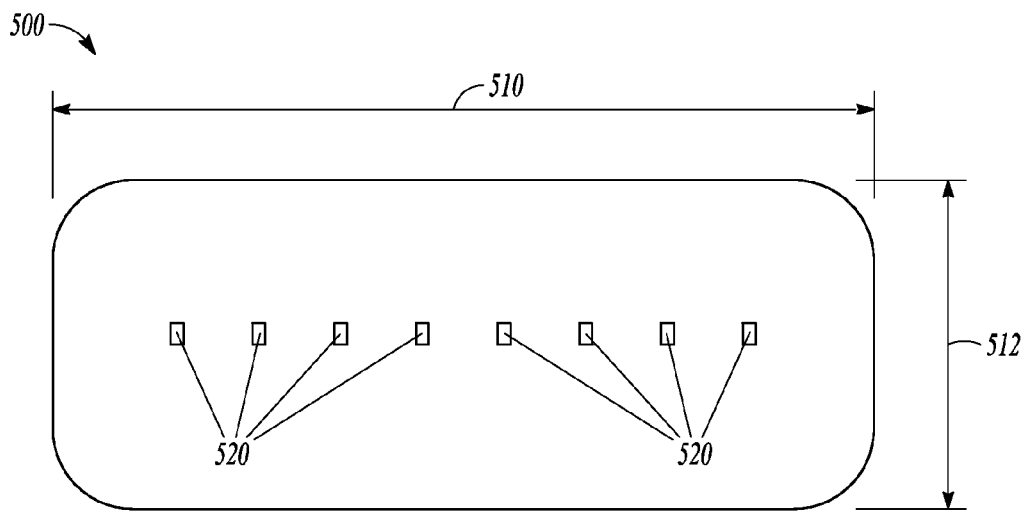
FIG. 5A is a top view of a patch according to an example embodiment.

FIG. 5A is a top view of a patch 500 according to an example embodiment. The patch 500 is substantially rectangular with rounded corners, although it may have another shape suited for placement in a mask. The patch 500 may comprise a flexible polyamide or paper or plastic material with integrated circuits and conductive lines or traces and terminals formed thereon (not shown). The patch 500 has a length 510, a width 512 and a thickness (not shown). The length 510 is approximately 1.5 inches and the width 512 is approximately 1 inch. FIG. 5A illustrates a skin side of the patch 500 to be in contact with the skin of the wearer. The patch 500 includes eight thermistors 520 on the skin side.

Figure 5B:
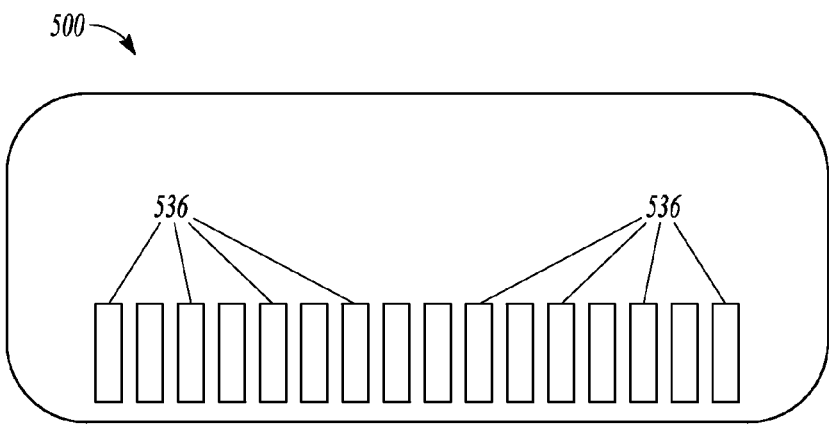
FIG. 5B is a bottom view of the patch shown in FIG. 5A according to an example embodiment.

FIG. 5B is a bottom view of the patch 500 shown in FIG. 5A according to an example embodiment. FIG. 5B illustrates an insulated side of the patch 500 that is exposed to the insulated or to a mask worn by the wearer. The patch 500 includes 16 electrical contacts 536 that may be metal pads to couple signals to and from the patch 500.

Figure 6:
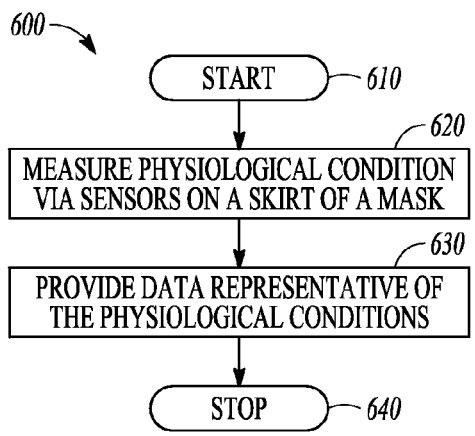
FIG. 6 is a flowchart illustrating a method according to an example embodiment.

FIG. 6 is a flowchart illustrating a method 600 according to an example embodiment. The method starts at 610, and at 620 the method measures physiological conditions of a wearer of a mask via sensors on a skirt of the mask proximate a forehead of the wearer. At 630, the method provides data representative of the measured physiological conditions of the wearer to circuitry to determine the condition of the wearer as a function of the provided data. The method ends at 640.

Figure 7:
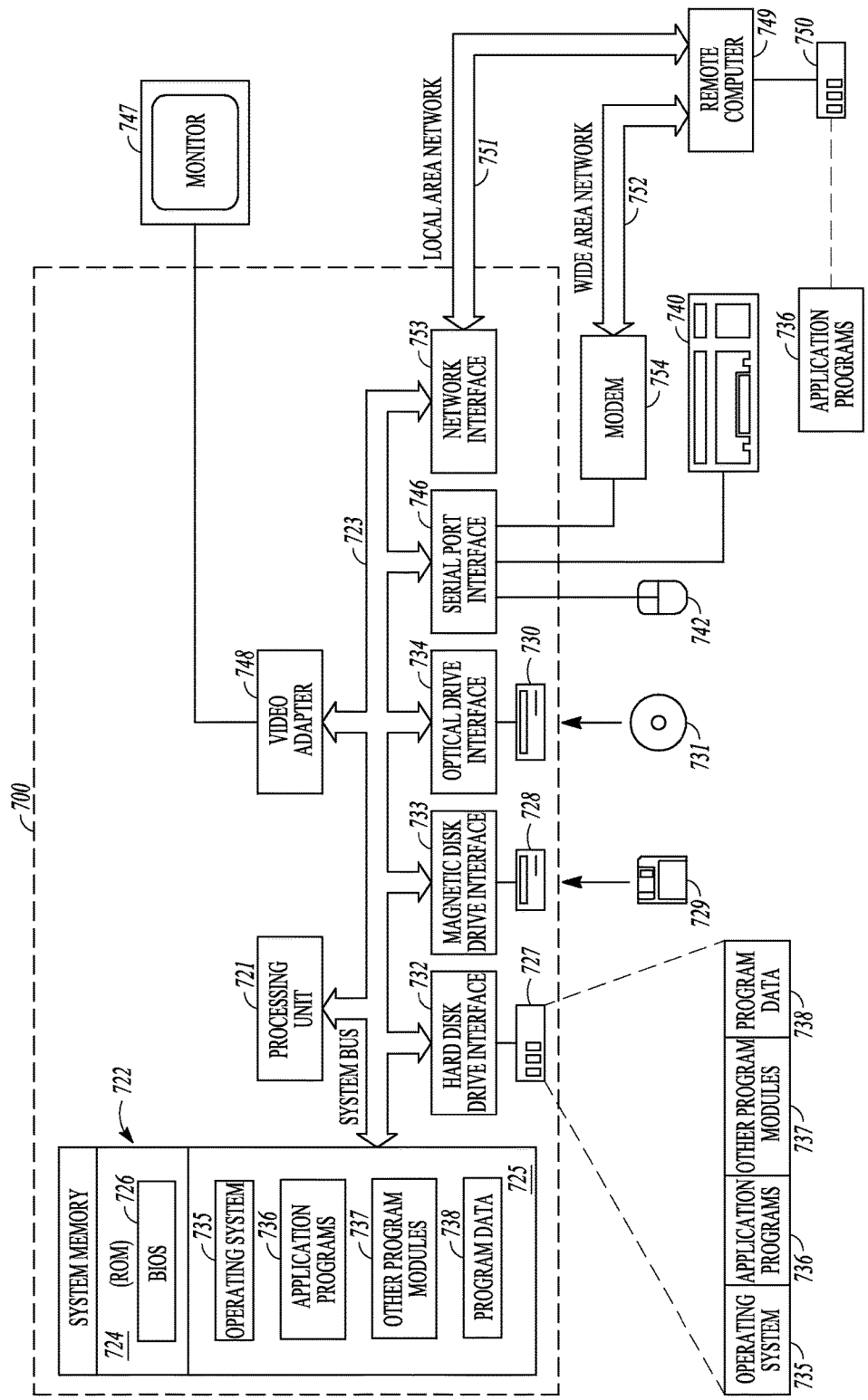
FIG. 7 is a block diagram of a computer system to analyze physiological data obtained from the integrated sensors.

FIG. 7 is a block diagram of a computer system to analyze physiological data obtained from the integrated sensors. While several optional components are illustrated, many are not needed to perform the methods and functions described above, and may be omitted in various embodiments.

As shown in FIG. 7, one embodiment of the hardware and operating environment includes a general purpose computing device in the form of a computer 700 (e.g., a personal computer, workstation, or server), including one or more processing units 721, a system memory 722, and a system bus 723 that operatively couples various system components including the system memory 722 to the processing unit 721. There may be only one or there may be more than one processing unit 721, such that the processor of computer 700 comprises a single central-processing unit (CPU), or a plurality of processing units, commonly referred to as a multiprocessor or parallel-processor environment. In various embodiments, computer 700 is a conventional computer, a distributed computer, or any other type of computer.

The system bus 723 can be any of several types of bus structures including a memory bus or memory controller, a peripheral bus, and a local bus using any of a variety of bus architectures. The system memory can also be referred to as simply the memory, and, in some embodiments, includes read-only memory (ROM) 724 and random-access memory (RAM) 725. A basic input/output system (BIOS) program 726, containing the basic routines that help to transfer information between elements within the computer 700, such as during start-up, may be stored in ROM 724. The computer 700 further includes a hard disk drive 727 for reading from and writing to a hard disk, not shown, a magnetic disk drive 728 for reading from or writing to a removable magnetic disk 729, and an optical disk drive 730 for reading from or writing to a removable optical disk 731 such as a CD ROM or other optical media.

The hard disk drive 727, magnetic disk drive 728, and optical disk drive 730 couple with a hard disk drive interface 732, a magnetic disk drive interface 733, and an optical disk drive interface 734, respectively. The drives and their associated computer-readable media provide non-volatile storage of computer-readable instructions, data structures, program modules and other data for the computer 700. It should be appreciated by those skilled in the art that any type of computer-readable media which can store data that is accessible by a computer, such as magnetic cassettes, flash memory cards, digital video disks, Bernoulli cartridges, random access memories (RAMs), read only memories (ROMs), redundant arrays of independent disks (e.g., RAID storage devices) and the like, can be used in the exemplary operating environment.

A plurality of program modules can be stored on the hard disk, magnetic disk 729, optical disk 731, ROM 724, or RAM 725, including an operating system 735, one or more application programs 736, other program modules 737, and program data 738. Programming for implementing one or more processes or methods described herein may be resident on any one or number of these computer-readable media.

A user may enter commands and information into computer 700 through input devices such as a keyboard 740 and pointing device 742. Other input devices (not shown) can include a microphone, joystick, game pad, satellite dish, scanner, or the like. These other input devices are often connected to the processing unit 721 through a serial port interface 746 that is coupled to the system bus 723, but can be connected by other interfaces, such as a parallel port, game port, or a universal serial bus (USB). A monitor 747 or other type of display device can also be connected to the system bus 723 via an interface, such as a video adapter 748. The monitor 747 can display a graphical user interface for the user. In addition to the monitor 747, computers typically include other peripheral output devices (not shown), such as speakers and printers.

The computer 700 may operate in a networked environment using logical connections to one or more remote computers or servers, such as remote computer 749. These logical connections are achieved by a communication device coupled to or a part of the computer 700; other types of communication devices may also be used. The remote computer 749 can be another computer, a server, a router, a network PC, a client, a peer device or other common network node, and typically includes many or all of the elements described above 110 relative to the computer 700, although only a memory storage device 750 has been illustrated. The logical connections depicted in FIG. 7 include a local area network (LAN) 751 and/or a wide area network (WAN) 752. Such networking environments are commonplace in office networks, enterprise-wide computer networks, intranets and the internet, which are all types of networks.

When used in a LAN-networking environment, the computer 700 is connected to the LAN 751 through a network interface or adapter 753, which is one type of communications device. In some embodiments, when used in a WAN-networking environment, the computer 700 typically includes a modem 754 (another type of communications device) or any other type of communications device, e.g., a wireless transceiver, for establishing communications over the wide-area network 752, such as the internet. The modem 754, which may be internal or external, is connected to the system bus 723 via the serial port interface 746. In a networked environment, program modules depicted relative to the computer 700 can be stored in the remote memory storage device 750 of remote computer, or server 749. It is appreciated that the network connections shown are exemplary and other means of, and communications devices for, establishing a communications link between the computers may be used including hybrid fiber-coax connections, T1-T3 lines, DSL's, OC-3 and/or OC-12, TCP/IP, microwave, wireless application protocol, and any other electronic media through any suitable switches, routers, outlets and power lines, as the same are known and understood by one of ordinary skill in the art.

Embodiments described and claimed herein are not to be limited in scope by the specific embodiments herein disclosed, since these embodiments are intended as illustration of several aspects of the disclosure. Any equivalent embodiments are intended to be within the scope of this disclosure. Indeed, various modifications of the embodiments in addition to those shown and described herein will become apparent to those skilled in the art from the foregoing description. Such modifications are also intended to fall within the scope of the appended claims.

The invention claimed is:

1. A human wearable mask comprising:
    a pliable skirt including a skin contacting portion for directly contacting a forehead of a human wearer; and
    a sensor applied along the skin contacting portion of the pliable skirt and projecting from the pliable skirt toward the forehead:
        the sensor configured to obtain and provide contact based temperature data from the forehead of the human wearer, and
        wherein deformable engagement of the skin contacting portion of the pliable skirt causes the skin contacting portion of the pliable skirt to bias the sensor projecting from the pliable skirt into direct contact with the forehead of the human wearer.

2. The mask of claim 1 and further comprising a transmitter communicatively coupled to the sensor to wirelessly transmit the sensed data.

3. The mask of claim 1 wherein the mask is a full face respirator.

4. The mask of claim 1 wherein the mask is a self-contained breathing apparatus mask.

5. The mask of claim 1 wherein the sensor further comprises a respiration rate sensor.

6. The mask of claim 1 wherein the sensor further comprises moisture sensor to sense presence of sweat.

7. The mask of claim 1 wherein the sensor further comprises pulse rate sensor.

8. The mask of claim 1 wherein the skirt is formed of silicone, and the sensor is formed on a flexible circuit patch positioned about the forehead of the human wearer.

9. The mask of claim 8 wherein the sensor comprises multiple thermistors aligned in a row such that a thermistor is positioned proximate a temporal artery of the human wearer to measure a temperature representative of the body core temperature of the human wearer.

10. The mask of claim 1 and further comprising processing circuitry to determine a condition of a wearer as a function of the sensed data.

11. The mask of claim 10 and further comprising a monitor to alert the wearer of the condition of the wearer.

12. A full face respirator comprising:
    a frame;
    a gas conduit supported by the frame;
    a pliable skirt coupled to the frame, the pliable skirt includes a skin contacting portion configured for directly contacting and deforming against a forehead of a human wearer to provide a seal with a face and forehead;
    a thermistor extending beyond the pliable skirt toward the forehead, the thermistor configured to obtain and provide temperature data from the forehead of the human wearer proximate a temporal artery of the human wearer; and
    wherein the deformation of the skin contacting portion causes the skin contacting portion of the pliable skirt to bias the thermistor into contact with the forehead of the human wearer.

13. The full face respirator of claim 12 and further comprising multiple thermistors supported on the skirt.

* * * * *